US005714463A

United States Patent [19]
York et al.

[11] Patent Number: 5,714,463
[45] Date of Patent: Feb. 3, 1998

[54] USE OF GROWTH FACTOR AND ANTIMETABOLITE COMBINATION TO PREVENT OR RETARD FISTULA CLOSURE FOLLOWING GLAUCOMA FILTRATION SURGERY

[75] Inventors: Billie M. York; Jon C. Nixon, both of Fort Worth, Tex.

[73] Assignee: Alcon Laboratories, Inc., Fort Worth, Tex.

[21] Appl. No.: 391,889

[22] Filed: Feb. 21, 1995

Related U.S. Application Data

[63] Continuation of Ser. No. 129,287, Sep. 29, 1993, abandoned.
[51] Int. Cl.$^6$ .......................... A61K 37/00; A61K 31/40
[52] U.S. Cl. ........................ 514/12; 814/413; 814/913
[58] Field of Search ........................... 514/12, 413, 913

[56] References Cited

U.S. PATENT DOCUMENTS

| | | | |
|---|---|---|---|
| 4,981,841 | 1/1991 | Gibson | 514/2 |
| 4,983,580 | 1/1991 | Gibson | 514/2 |
| 5,061,786 | 10/1991 | Burnier et al. | 530/326 |
| 5,108,989 | 4/1992 | Amento et al. | 514/12 |
| 5,124,392 | 6/1992 | Robertson et al. | 524/427 |

FOREIGN PATENT DOCUMENTS

| | | | |
|---|---|---|---|
| 0 190 018 | 8/1986 | European Pat. Off. | 37/2 |
| WO 94/01124 | 1/1994 | WIPO | 37/2 |

OTHER PUBLICATIONS

Tahery, M. M., et al., "Pharmacologic Control of Wound Healing in Glaucoma Filtration Surgery", *Journal of Ocular Pharmacology*, vol. 5, No. 2, pp. 155–179 (1989).

Tripathi, R.C., et al., "Growth Factors in the Aqueous Humor and Their Therapeutic Implications in Glaucoma and Anterior Segment Disorders of the Human Eye", *Drug Development Research*, vol. 22, pp. 1–23 (1991).

*Textbook of Glaucoma* (2nd ed.), ed. M. Bruce Shields, M.D., "Glaucoma Filtering Procedures", Chapter 34, pp. 461–487, Baltimore, MD; Williams & Wilkins (1987).

Connor Jr., T. B., et al., "Correlation of Fibrosis and Transforming Growth Factor—B Type 2 Levels in the Eye", *The American Society for Clinical Investigation, Inc.*, vol. 83, pp. 1661–1666 (May 1989).

Costa, V. P., et al., "Wound Healing Modulation in Glaucoma Filtration Surgery", *Ophthalmic Surgery*, vol. 24, No. 3, pp. 152–170 (Mar. 1993).

Gillies, M. C., et al., "Cytokines, fibrosis and the failure of glaucoma filtration surgery", *Australian and New Zealand Journal of Ophthalmology*, vol. 19, No. 4, pp. 299–304 (1991).

Van Buskirk, E. M., "Mechanisms and management of filtration bleb failure", *Australian and New Zealand Journal of Ophthalmology*, vol. 20, No. 3, pp. 157–162 (1992).

Ophir, A., "Encapsulated Filtering Bleb", *Eye*, vol. 6, pp. 348–352 (1992).

Joseph, J. P., et al., "Wound Healing as a Barrier to Successful Filtration Surgery", *Eye*, 2 Suppl., pp. 113–123 (1988).

Jampel, H. D., "Impact of Adjuvant Chemotherapy on Glaucoma Filtration System", *Journal of Glaucoma*, vol. 2, 1993 Raven Press Ltd., pp. 58–63.

Skuta, G. L., et al., "Wound Healing in Glaucoma Filtering Surgery", *Survey Of Ophthalmology*, vol. 32, No. 3, pp. 149–170 (Nov.–Dec. 1987).

Schultz, G., et al., "Effects of Growth Factors on Corneal Wound Healing", *ACTA Ophthalmologica*, vol. 70, Suppl. 202, pp. 60–66 (1992).

Amento, E. P., et al., "TGF–B and wound healing", *Wiley, Chichester, Ciba Foundation Symposium 157*, pp. 115–129 (1991).

Schreier, T., et al., *Research in Experimental Medicine*, "Fibroblast migration and proliferation during in vitro wound healing", vol. 193, No. 4, pp. 195–205 (Aug. 1993).

Hendriks, T., et al., *British Journal of Cancer*, "Inhibition of basal and TGFβ–induced fibroblast collagen synthesis by antineoplastic agents. Implications for wound healing", vol. 67, No. 3, pp. 545–550 (Mar. 1993).

*Primary Examiner*—Zohreh Fay
*Attorney, Agent, or Firm*—Gregg C. Brown

[57] ABSTRACT

The intraocular use of combinations of stromal cell growth stimulators (e.g., TGF-β) and antimetabolites (e.g., mitomycin C) in connection with glaucoma filtration surgery is described. The combination is applied to the surgical site to attract, mitogenically activate, and neutralize the potential for extracellular matrix synthesis leading to scar formation by stromal cells. Without such treatment, the formation of scar tissue may lead to impairment of the outflow of aqueous humor at the surgical site, particularly the fistula. The mitogenic activation of the stromal cells makes these cells susceptible to the anti-metabolites. This enables the antimetabolites to suppress the proliferation of the fibroblasts and other associated stromal cells to a much greater extent, relative to the proliferation seen when the metabolites alone are utilized. The increased suppression of the proliferation and metabolism of these cells results in a significant improvement in the ability to prevent or retard the formation of scar tissue, and thereby reduces the incidence of fistula closure following glaucoma filtration surgery.

7 Claims, No Drawings

USE OF GROWTH FACTOR AND ANTIMETABOLITE COMBINATION TO PREVENT OR RETARD FISTULA CLOSURE FOLLOWING GLAUCOMA FILTRATION SURGERY

This is a continuation of application Ser. No. 08/129,287, filed Sep. 29, 1993, now abandoned.

BACKGROUND OF THE INVENTION

The present invention relates to the field of ophthalmology. More specifically, the invention relates to the field of glaucoma filtration surgery.

The underlying causes of glaucoma are not fully understood. However, it is known that a principal symptom of this disease is elevated intraocular pressure. Elevations of intraocular pressure can ultimately lead to impairment or loss of normal visual function as a result of damage to the optic nerve. It is also known that the elevated intraocular pressure is caused by an excess of fluid (i.e., aqueous humor) within the eye. The excess intraocular fluid is believed to result from blockage or impairment of the normal drainage of fluid from the eye via the trabecular meshwork.

The current drug therapies for treating glaucoma attempt to control intraocular pressure by means of increasing the drainage or "outflow" of aqueous humor from the eye or decreasing the production or "inflow" of aqueous humor by the ciliary processes of the eye. Unfortunately, the use of drug therapy alone is not sufficient to adequately control intraocular pressure in some patients, particularly if there is a severe blockage of the normal passages for the outflow of aqueous humor. Such patients may require surgical intervention to restore the normal outflow of aqueous humor and thereby normalize or at least control their intraocular pressure. The outflow of aqueous humor can be improved by means of various intraocular surgical procedures known to those skilled in the art, such as trabeculectomy, posterior lip sclerectomy, trephine and thermal sclerostomy. These surgical procedures are collectively referred to herein as "glaucoma filtration surgery".

The procedures utilized in glaucoma filtration surgery generally involve the creation of a fistula to promote the drainage of aqueous humor. Although various procedures have been utilized, the procedures will typically include the creation of an elevation of the conjunctiva at the surgical site. This elevation is commonly referred to as the "filtering bleb". The filtering blebs which are most often associated with good intraocular pressure control are avascular and either low and diffuse or elevated with numerous cystic spaces. Studies have suggested that aqueous fluid in the filtering bleb usually filters through the conjunctiva and mixes with the tear film, or is adsorbed by vascular or perivascular conjunctival tissue.

Although glaucoma filtration surgery is generally successful initially, it is often plagued by the formation of scar tissue which may ultimately block the fistula created during the surgery. The following articles may be referred to for further background information concerning this problem:

1) Tahery, M. M., et al., "Pharmacologic Control of Wound Healing in Glaucoma Filtration Surgery", *Journal of Ocular Pharmacology*, Vol. 5, No. 2, pages 155–179 (1989);

2) Tripathi, R. C., "Growth Factors in the Aqueous Humor and Their Therapeutic Implications in Glaucoma and Anterior Segment Disorders of the Human Eye", *Drug Development Research*, Vol. 22, pages 1–23 (1991); and 3) *Textbook of Glaucoma* (2nd ed.), ed. M. Bruce Shields, M.D., "Glaucoma Filtering Procedures", Chapter 34, pages 461–487, Baltimore Md.: Williams & Wilkins (1987).

The most common cause of failure in glaucoma filtration surgery is closure of the fistula as the result of scar tissue formation and other manifestations of the normal wound healing process. The increased amount of collagen in the failed fistulas suggests that proliferation of fibroblasts and associated production of extracellular matrix materials, particularly collagen, fibronectin and glycosaminoglycans, may lead to fistula failure.

As indicated in the above-cited article by Tahery, et al., the use of drugs to inhibit or control the wound healing process, and thereby limit the formation of scar tissue in glaucoma filtration surgery, has been previously proposed. The article mentions various types of drugs as potential inhibitors of the wound healing process, including antiinflammatory drugs and anti-proliferative drugs. However, the use of such drugs to prevent scar formation associated with glaucoma filtration surgery has had very limited success. One reason for this lack of success is that the wound healing process does not take place instantaneously. Consequently, it is not possible to simply prevent scar formation by means of a single application of the drugs at the time of surgery. Moreover, many drugs, when utilized at higher concentrations to prevent scar formation, are inherently toxic to other ophthalmic tissues not directly involved in the surgically induced wound healing process. This potential toxicity precludes the use of higher drug concentrations which might otherwise be considered useful in controlling or at least suppressing the formation of extracellular matrix and scar tissue associated with wound closure following glaucoma filtration surgery. Moreover, even with the use of antiproliferative agents such as 5'-fluorouracil, the failure rate (i.e., total blockage of fistula) in high-risk groups, such as patients with previous failed filtering surgery, previous cataract extraction, aphakia, or neovascular glaucoma, is still significant. In addition, many of the antiproliferative drugs used may be associated with complications such as corneal or conjunctival epithelial loss, corneal opacification, and the possibility of long-term wound leaks and endophthalmitis related to extremely thin blebs which can occur with drug treatment. The use of single-dose, intra-operative exposures to antiproliferative agents such as mitomycin C may reduce some of these problems, but the problems with thin blebs and hypotony will still exist.

In view of the foregoing circumstances, there is a need for an improved drug therapy to complement glaucoma filtration surgery, so that the enhanced outflow of aqueous humor achieved by means of the surgery is not ultimately lost as the result of closure of the surgical fistula by scar tissue. The present invention is directed to satisfying this need.

SUMMARY OF THE INVENTION

The present invention provides a method to prevent or retard scar formation associated with glaucoma filtration surgery, and thereby reduce the incidence of fistula closure. The method is based on the application of a composition which contains a combination of one or more stromal cell growth stimulators and an antimetabolite to the surgical site at the time of surgery. Various stromal cell growth stimulators or combinations thereof may be utilized for this purpose, but the most preferred approach is to utilize a combination which includes transforming growth factor-beta ("TGF-β").

Although applicants do not desire to be bound by any theory, it is believed that the stromal cell growth stimulator component of the present invention both mitogenically activates fibroblasts and attracts fibroblasts to the surgical site. The mitogenic activation of fibroblasts renders these cells susceptible to growth suppression by the antimetabolite component of the present invention. Similarly, the stromal cell growth stimulator/antimetabolite combination of the present invention also reduces the number of monocytes present at the surgical site. The presence of monocytes which give rise to macrophages at the surgical site is generally desirable due to their function in natural debridement and extracellular matrix restructuring of the surgical wound. However, these cells also release growth factors which contribute to a cascade of cell stimuli leading to rapid synthesis of extracellular matrix materials and scar formation. Suppression of the entry of these cells into the wound site is therefore desirable.

The above-described method results in a greater reduction in extracellular matrix synthesis and scar formation, as compared to the reduction achieved with an antimetabolite alone. The method also enables a lower concentration of antimetabolite to be utilized. As a result, the method provides a significant improvement in the ability to prevent or retard the formation of scar tissue and reduce the incidence of fistula closure in glaucoma filtration surgery.

DESCRIPTION OF PREFERRED EMBODIMENTS

The stromal cell growth stimulators which may be utilized in the present invention include all agents which will mitogenically activate cells within the sclera, stroma and Tenon's capsule, and thereby initiate DNA synthesis in those cells. The cells targeted for such activation are predominantly fibroblasts, but other cells may also be involved in the stromal wound healing process. The fibroblasts, monocytes migrating into the wound, and other cells associated with the wound healing process are collectively referred to herein as "stromal cells". Growth factors or other agents which mitogenically activate stromal cells are referred to herein as "stromal cell growth stimulators". The preferred stromal cell growth stimulators are mixtures of growth factors which include various isoforms of TGF-$\beta$.

There are five known isoforms of TGF-$\beta$. These forms have been designated as TGF-$\beta_1$, TGF-$\beta_2$, TGF-$\beta_3$, TGF-$\beta_4$ and TGF-$\beta_5$, the first three being common to man. The physical properties of these growth factors, sources of same, and methods of purification are known. See, for example, U.S. Pat. No. 5,108,989 (Amento, et al; Genentech, Inc.) and the references cited therein at lines 21–45 of column 1. The entire contents of that patent relating to the various forms of TGF-$\beta$ are hereby incorporated by reference in the present specification. As utilized herein, the term "TGF-$\beta$" encompasses one or more polypeptides having the ability to attract fibroblasts and monocytes to the surgical site and mitogenically activate these cells, such as: mature and precursor forms of TGF-$\beta_1$, TGF-$\beta_2$, TGF-$\beta_3$, TGF-$\beta_4$ and TGF-$\beta_5$; hybrid TGF-$\beta$s; latent TGF-$\beta$ complexes; TGF-$\beta$ analogs (e.g., deletion variants); and biologically active polypeptides based on transforming growth factor-beta sequences, such as those described in U.S. Pat. No. 5,061,786 (Burnier, et al.; Genentech, Inc.).

The stromal cell growth stimulators which may be utilized in the present invention also include transforming growth factor-alpha (TGF-$\alpha$), keratinocyte growth factor ("KGF"), epidermal growth factor ("EGF"), platelet-derived growth factor ("PDGF"), basic fibroblast growth factor ("b-FGF"), acid fibroblast growth factor ("a-FGF"), angiogenin, nerve growth factor ("NGF"), insulin-like growth factor I and II ("IGF-I" and "IGF-II"), and other proteins or polypeptides having chemo-attractant and mitogenic stimulant activity relative to stromal cells. As used herein, the term "polypeptides" encompasses natural, synthetic and recombinant polypeptides, including polypeptides having deleted, replaced or altered amino acid sequences in comparison with the full-length natural polypeptide or biologically active fragments thereof.

The stromal cell growth stimulators utilized in the present invention are preferably human derived. As used herein, the term "human derived" encompasses both agents recovered from human tissues and agents produced from human cell lines by means of recombinant DNA technology.

The compositions utilized in the present invention contain one or more of the above-described stromal cell growth stimulators in an amount sufficient to attract fibroblasts, monocytes and other stromal cells to the surgical site and mitogenically activate these cells. In general, the concentration required to achieve this purpose is approximately 10 to 100 times less than the concentration required to stimulate the proliferation of stromal cells. The amount of stromal cell stimulator required for this purpose will vary depending on the particular agent or agents utilized, but will generally be from about 10 picograms per milliliter ("pcg/ml") to about 50 micrograms per milliliter ("mcg/ml").

The compositions utilized in the present invention will also include one or more antimetabolites to suppress the proliferation of stromal cells within the wound created by glaucoma filtration surgery, particularly the fistula. Various antimetabolites may be utilized for this purpose. The antimetabolites which may be utilized can be generally characterized as being structural analogs to metabolically active molecules, such as purines, pyrimidines and folic acid. These compounds interfere with normal DNA/RNA synthesis, and thereby disrupt cellular function. The net effects of this action are reduced mitotic activity and, ultimately, decreased cell proliferation. Examples of antimetabolites which may be utilized in the present invention include mitomycin C, 5'-fluorouracil, arabinocytosine, taxol, actinomycin C, and methotrexate. The use of mitomycin C as the antimetabolite component of the present invention is preferred, because it is relatively less toxic to corneal endothelial cells than other antimetabolites, such as 5'-fluorouracil.

The compositions utilized in the present invention contain one or more of the above-described antimetabolites in an amount sufficient to suppress the growth of stromal cells in the wound environment, particularly in the fistula. The amount of antimetabolite required for this purpose will vary depending on the particular antimetabolite(s) selected, but will generally be from about 0.01 to about 500 micrograms/ milliliter ("mcg/ml").

The above-described combinations of stromal cell growth stimulators and antimetabolites can be included in various types of pharmaceutical vehicles suitable for intraocular use. The vehicles are preferably aqueous, and are formulated so as to be chemically and physically compatible with ophthalmic tissues. For example, the stromal cell growth simulator/antimetabolite combination may be included in aqueous irrigating solutions, bioerodible gels or collagen inserts. The use of such gels or inserts has the advantage of providing sustained release of the active components at the surgical site. However, the use of an aqueous solution as the vehicle for the stromal cell growth stimulator/antimetabolite combination may be preferred in some cases due to the potential for blockage of the filtering bleb by erodible gels or other solid or semi-solid inserts. The aqueous solutions which might be utilized must be compatible with intraocular tissues, and should preferably help to maintain the integrity and function of intraocular tissues during the surgical procedure. The aqueous solutions which might be utilized for the above-described purposes include balanced saline solutions, such as BSS® Balanced Salt Solution and BSS Plus® Balanced Salt Solution Enriched with Bicarbonate, Dextrose and Glutathione, both of which are available from Alcon Surgical, Inc., Fort Worth, Tex.

As will be appreciated by those skilled in the art, the above-described compositions must be sterile and should not include any agents (e.g., antimicrobial preservatives) which will be toxic to sensitive intraocular tissues, particularly cornea/endothelial cells. The above-described compositions can be formulated in accordance with techniques known to those skilled in the art.

The above-described compositions can be applied to the surgical site by means of various techniques. For example, the compositions can be applied by means of a syringe during or immediately after surgery. The only critical requirement with respect to how the compositions are applied is that the compositions be distributed throughout the surgical site, particularly the fistula, and remain in contact with the surgical site for a length of time sufficient to suppress the growth and chemotaxis of stromal cells, particularly fibroblasts and monocytes. The amount of time required to achieve this purpose will vary somewhat depending on circumstances such as the particular stromal cell growth stimulators and antimetabolites utilized, and the method by which the stromal cell growth stimulator/ antimetabolite combination is applied to the surgical site. However, the compositions will generally need to remain in contact with cells in the surgically-created fistula for at least five to ten minutes. The above-described compositions may be removed by irrigation and aspiration. Multiple applications during and after the glaucoma filtration surgery procedures may be desirable or necessary in some cases.

What is claimed is:

1. A method of reducing the formation of scar tissue following glaucoma filtration surgery, which comprises applying to the surgical site at the time of surgery a composition comprising: a stromal cell growth stimulator in an amount sufficient to attract and mitogenically activate stromal cells at the surgical site; an antimetabolite in an amount sufficient to suppress the proliferation of the stromal cells; and a pharmaceutically acceptable vehicle therefor, thereby further reducing extracellular matrix synthesis and scar formation at the surgical site, relative to the reduction achieved with the antimetabolite alone.

2. A method according to claim 1, wherein the stromal cell growth stimulator is human derived.

3. A method according to claim 1, wherein the stromal cell growth stimulator comprises a growth factor.

4. A method according to claim 3, wherein the growth factor comprises TGF-β.

5. A method according to claim 1, wherein the antimetabolite is selected from the group consisting mitomycin C, 5'-fluorouracil, arabinocytosine, taxol, actinomycin C and methotrexate.

6. A method according to claim 5, wherein the antimetabolite comprises mitomycin C.

7. A method according to claim 1, wherein the composition comprises the stromal cell growth stimulator in an amount of 10 pcg/ml to 50 mcg/ml and the antimetabolite in an amount of 0.01 to 500 mcg/ml.

* * * * *